United States Patent [19]

Tsien et al.

[11] Patent Number: 4,689,432

[45] Date of Patent: Aug. 25, 1987

[54] CHELATORS WHOSE AFFINITY FOR CALCIUM IS DECREASED BY ILLUMINATION

[75] Inventors: Roger Y. Tsien, Berkeley, Calif.; Grzegorz Grynkiewicz, Warszawa, Poland; Akwasi Minta, Albany, Calif.

[73] Assignee: The Regents of the University of California, Berkeley, Calif.

[21] Appl. No.: 648,536

[22] Filed: Sep. 7, 1984

[51] Int. Cl.$^4$ .................. C07C 101/26; C07D 215/38
[52] U.S. Cl. .................................... 562/435; 546/23; 546/171; 549/220; 549/336; 549/439; 558/44; 560/21; 424/DIG. 6
[58] Field of Search .......................... 560/21; 562/435; 549/439, 220, 366; 546/171, 23; 558/44

[56] References Cited

PUBLICATIONS

Henry A. Lester and Jeanne M. Nerbonne "Physiological and Pharmacological Manipulations with Light Flashes", Div. of Biology 156-29, California Institute of Technology, Pasadena, Calif. 91125, Ann. Rev. Biophys. Bioeng. 1982:11-151-75.

A. Patchornik, "Photosensitive Protecting Groups", Journ. of the American Chemical Society, 92:21, Oct. 21, 1970.

Roger Y. Tsien, "New Calcium Indicators and Buffers with High Selectivity against Magnesium and Protons: Design, Synthesis, and Properties of Prototype Structures", Am. Chem, Soc. 1980.

Roger Y. Tsien, "Intracellular Measurements of Ion Activities", Ann. Rev. Biophys. Bioeng., 12:91-116, 1983.

*Primary Examiner*—Dolph H. Torrence
*Attorney, Agent, or Firm*—Fitch, Even, Tabin & Flannery

[57] ABSTRACT

The present invention discloses a group of calcium chelating compounds which have a descreased affinity for calcium following illumination. These new compounds contain a photolabile nitrobenzyl derivative coupled to a tetracarboxylate $Ca^{2+}$ chelating parent compound having the octacoordinate chelating groups characteristic of EGTA or BAPTA. In a first form, the new compounds are comprised of a BAPTA-like chelator coupled to a single 2-nitrobenzyl derivative, which in turn is a photochemical precursor of a 2-nitrosobenzophenone. In a second form, the new compounds are comprised of a BAPTA-like chelator coupled to two 2-nitrobenzyl derivatives, themselves photochemical prcursors of the related 2-nitrosobenzophenones.

The present invention also discloses a novel method for preparing 1-hydroxy- or 1-alkoxy-1-(2-nitroaryl)-1-aryl methanes. Methanes of this type are critical to the preparation of, or actually constitute, the photolabile $Ca^{2+}$ chelating compounds disclosed and claimed herein.

13 Claims, 8 Drawing Figures

25 μM nitr-2 after illumination
Ca²⁺ titration

Aplysia neuron L2 injected with nitr-2 slightly hyperpolarizes on illumination

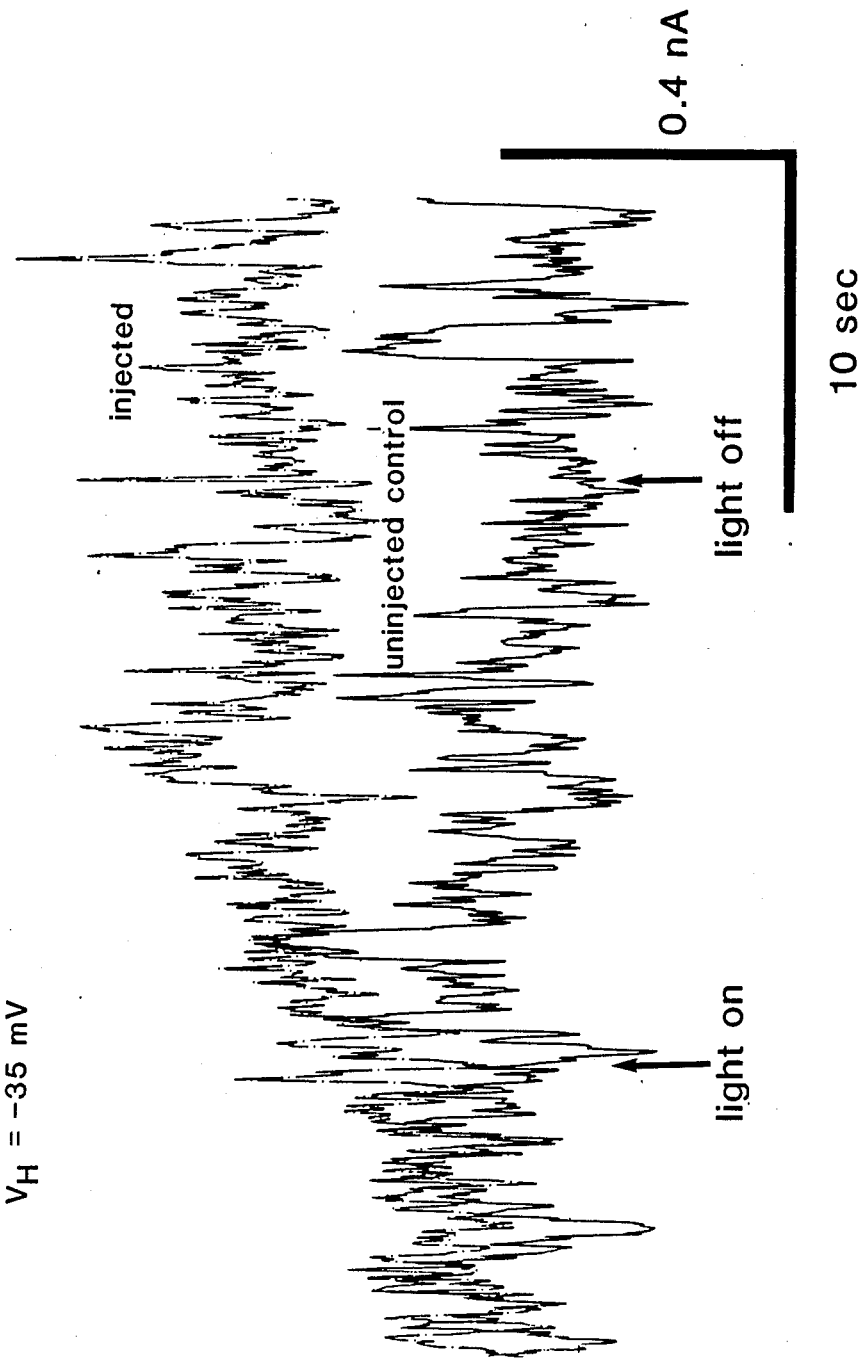

CHELATORS WHOSE AFFINITY FOR CALCIUM IS DECREASED BY ILLUMINATION

This invention was made with Government support under Grant NAGW-515 awarded by NASA. The Government has certain rights in this invention.

FIELD OF THE INVENTION

The present invention relates to photolabile $Ca^{2+}$ chelators whose affinity for calcium is decreased by illumination. The present invention also relates to a novel method for preparing 1-hydroxy- or 1-alkoxy-1-(2-nitroaryl)-1-aryl methanes. Methanes of this type are either critical to the preparation of, or actually constitute, the photolabile $Ca^{2+}$ chelating compounds disclosed and claimed herein.

BACKGROUND OF THE INVENTION

One of the most dynamic areas of modern cell biology is the study of the functions of calcium ions inside cells. Calcium is already known to control the contraction of all known types of muscle, the secretion of hormones from gland cells and transmitters from nerve synapses, plus a multitude of other functions (see Campbell, 1983). Calcium is also suspected, but not yet proven, to be at the center of some of the biggest remaining mysteries in biology, e.g., how a cell decides when to grow and divide, how non-muscle cells control their own movements, and how the nervous system stores learned patterns and memories. For example, the two most recent theories of the molecular mechanism of neuronal learning (see Kandel, 1981 and Lynch, et al., 1984) differ in most aspects but agree in postulating that minute localized fluctuations in cytostolic free calcium levels inside nerve synapses are the key link between long-term biochemical changes and the efficiency of information transfer at those synapses. To study these important physiological processes, it would be extremely useful to produce similar fluctuations in free calcium levels by independent experimental means. This would show to what extent the natural events could be mimicked or elicited in response to properly controlled calcium changes.

The present invention describes novel compounds that store $Ca^{2+}$ in a physiologically inactive form until illuminated with ultraviolet light, whereupon the $Ca^{2+}$ tends to be released and is free to activate physiological processes. The use of light to control the release offers tremendous advantages because the intensity, position, spatial extent, and duration of a light beam can be conveniently manipulated with great precision. By contrast, the only general means previously available for raising $Ca^{2+}$ inside cells was to administer certain antibiotics extracted from fungi. These drugs, for example A23187 and ionomycin, act by transporting $Ca^{2+}$ across cell membranes, but cannot be controlled in precise locale and duration of action, and have major toxic side effects.

The need for photolabile $Ca^{2+}$ chelators of the type disclosed herein has been acknowledged by scientific investigators. For example, in a recent review of physiological and pharmacological manipulations with light flashes, Lester and Nerbonne (see Lester, et al., 1982) discuss both the need for such photolabile substances and their own unsuccessful attempts to synthesize a photosensitive chelator comprised of a photoisomerizable azobenzene group and an known calcium chelator such as EDTA and EGTA.

OBJECTS OF THE INVENTION

It is an object of the present invention to provide a new class of photolabile $Ca^{2+}$ chelators whose affinity for calcium is decreased by illumination.

It is a further object of the present invention to provide a method for preparing 1-hydroxy-or 1-alkoxy-1-(2-nitroaryl)-1-aryl methanes.

Other objects of the invention will become apparent to those skilled in the art from the following description, taken in connection with the accompanying drawings.

SUMMARY OF THE DRAWINGS

FIG. 8 is a time-voltage plot illustrating that illumination of a nitr-2 injected neuron elicits an outward current.

DEFINITION OF TERMS USED HEREIN

Figure 1:
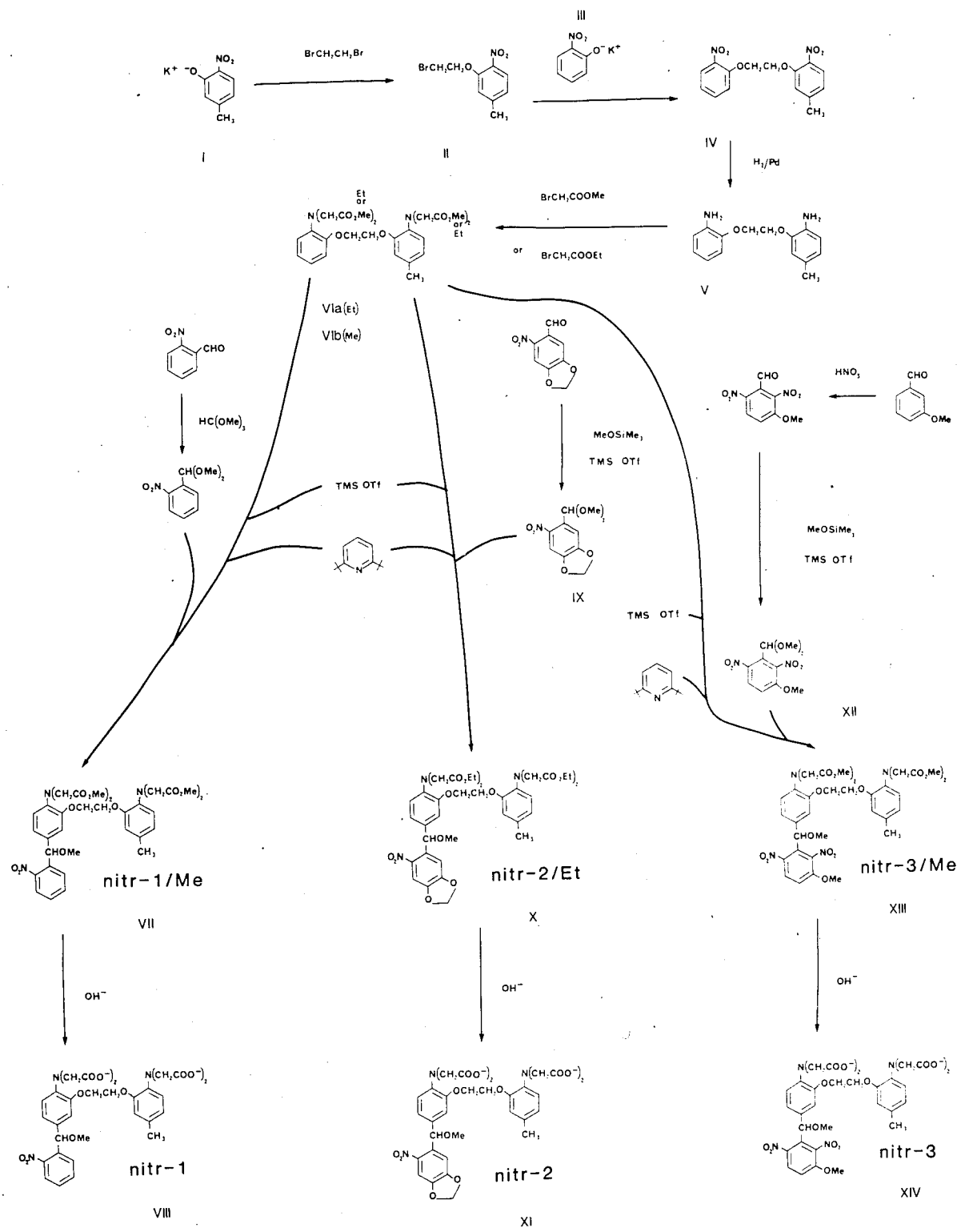
FIG. 1 is a chemical flow chart illustrating the synthetic pathway leading to nitr-1, nitr-2 and nitr-3.

The new photolabile $Ca^{2+}$ chelators disclosed herein are named with hyphens to distinguish the number 1 from the letter l, e.g., nitr-1, nitr-2, nitr-3, etc.

The chemical formulas for some of the compounds discussed herein are identified with Roman numerals These Roman numerals are used thoughout the specification (see especially, the Detailed Description of the Invention section, infra) as a shorthand means of identifying these compounds.

As used herein, nitr 1 means a compound comprised of 1-(2-amino-5-(1-methoxy-1-(2-nitrophenyl)methyl)-phenoxy)-2-(2'-amino-5'-methylphe noxy)ethane-N,N,N',N' tetraacetic acid. Nitr-1 is referred to herein as compound VIII.

As used herein, nitr-2 means a compound comprised of 1-(2-amino-5-(1-methoxy-1-(2-nitro-4,5-methylenedioxyphenyl)methyl)phenoxy)-2-(2'-amino-5'-methylphenoxy)-ethane-N,N,N',N' tetraacetic acid. Nitr-2 is referred to herein as compound XI.

As used herein, nitr-3 means a compound comprised of 1-(2-amino-5-(1-methoxy-1-(2,6-dinitro-3-methoxyphenyl)methyl)phenoxy)-2-(2'-amino-5'-methyl-phenoxy)-ethane-N,N,N',N' tetraacetic acid. Nitr-3 is referred to herein as compound XIV.

As used herein, TMS triflate or TMS-OTf means trimethylsilyl trifluoromethanesulfonate.

As used herein, MOPS means 3-(N-morpholino)propanesulfonic acid.

As used herein, EGTA means ethylene glycol bis(-beta-aminoethyl ether)-N,N,N',N'-tetracetic acid.

As used herein, BAPTA means 1,2-bis(2-aminophenoxy)ethane N,N,N',N'-tetraacetic acid; the chemical structure for BAPTA is:

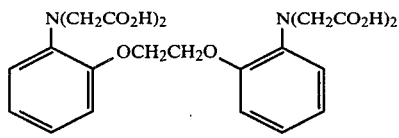

As used herein, quin1 means 2-[[2-[bis(carboxymethyl)amino]-5-methylphenoxy]-methyl]-8-[bis(carboxymethyl)amino]-quinoline.

As used herein, quin2 means 2-[[2-[bis(carboxymethyl)amino]-5-methylphenoxy]-methyl]-6-methoxy-8-[bis(carboxymethyl)amino]-quinoline; the chemical structure for quin2 is:

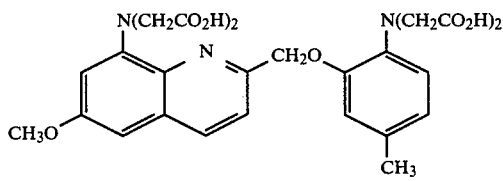

As used herein, BAPTA-like means substituted derivatives of BAPTA which retain the essential characteristic of two bis(carboxymethyl)amino-substituted phenyl rings, said rings being linked at the positions ortho to the amines through a four atom bridge wherein the atom adjacent to each phenyl ring is N or O and the two center atoms are each C. By this definition, it is meant that "BAPTA-like" includes compounds like quin-1 and quin-2.

As used herein, pharmaceutically acceptable esters mean those readily hydrolyzable esters which are known and used in the pharmaceutical industry, especially alpha-acyloxyalkyl esters. See generally, Ferres (1980) and Wermuth (1980).

As used herein, pharmaceutically acceptable non-toxic salts mean carboxylic acid salts wherein the counterion or ions are all Na, K, $NR_4^+$ (where R=H, $C_1$-$C_4$ alkyl or a mixture thereof), Ca, or Mg, or some combination of these counterions, or some combination of acid salts or these counterions plus free acid groups.

As used herein, $[Ca^{2+}]_i$ means intracellular free calcium.

As used herein, microM means micromolar.

Temperatures herein are given in degrees Centigrade.

REFERENCE LIST

The scientific publications cited herein are expressly incorporated by reference.

1. Campbell, A. K., (1983) *Intracellular Calcium*, Wiley, New York.
2. Kandel, E. R., (1981) *Nature* 293:697-700.
3. Lynch, G. and Baudry, M., (1984) *Science* 224:1057-1063.
4. Lester, H. and Nerbonne, J., (1982) *Ann. Rev. Biophys. Bioeng.* 11:151-175.
5. Tsien, R. Y., (1980) *Biochemistry* 19:2396-2404.
6. Noyori, R., Murata, S. and Suzuki, M., *Tetrahedron* 37:3899-3910.
7. Marsh, J. P., et al., (1965) *J. Org. Chem.* 30:2491-2492.
8. Freifelder, M., (1971) *Practical Catalytic Hydrogenation*, Wiley, New York.
9. Noyori, R., (1982) *Tetrahedron* 37:3899.
10. March, J., (1977) *Advanced Organic Chemistry*, Second Edition, McGraw Hill at pp. 498-499.
11. Meech, R. W., (1978) *Ann. Rev. Biophys. Bioeng.* 7:1-18.
12. Hatchard and Parker, (1956) *Proc. Roy. Soc. Lond.* A235:528.
13. Knoevenagel, E. (1913), *Liebigs Annalen der Chemie*, 402, 111-148.
14. Brown, G. H., editor, *Techniques of Chemistry*, Vol. III, Wiley-Interscience, New York. (1971). See "Photochromism" at pp. 34-37.

DESCRIPTION OF THE INVENTION

Brief Description of the Invention

The present invention comprises a new class of compounds which, when illuminated, decrease their affinity for calcium. The compounds contain a photolabile nitrobenzyl derivative coupled to a tetracarboxylate parent compound having the octacoordinate chelating groups characteristic of EGTA or BAPTA.

In a first form, the new compounds are comprised of a BAPTA-like chelator coupled to a single 2-nitrobenzyl derivative, which in turn is a photochemical precursor of a 2-nitrosobenzophenone. In this form, the new compounds are comprised of a chemical compound having the generic formula:

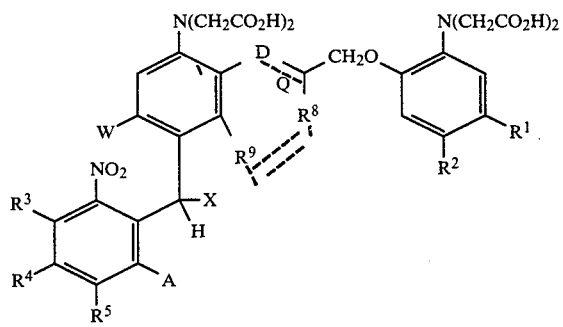

and the pharmaceutically acceptable non-toxic salts and esters thereof wherein:

A is $-NO_2$ or $-H$;

$R^1$ is selected from the group comprised of $-H$ (unless $R^2$ is also H), $-CH_3$, $-F$, $-Cl$, and $-Br$;

$R^2$ is selected from the group comprised of $-H$ (unless $R^1$ is also H), $-CH_3$, $-F$, $-Cl$, $-Br$, and $C_1$-$C_4$ alkoxy;

$R^3$, $R^4$ and $R^5$ are independently $-H$, OH, $NR^6R^7$, or alkoxy, or $R^3$ and $R^4$ together are $-OCH_2O-$ or $-OCH_2CH_2O-$ and $R^5$ is $-H$, OH, $NR^6R^7$, or alkoxy, or $R^4$ and $R^5$ together are $-OCH_2O-$ or $OCH_2CH_2O-$ and $R^3$ is $-H$, OH, $NR^6R^7$, or alkoxy;

X is selected from the group comprised of $-OH$, alkoxy, $-Cl$, $-Br$, $-NR^6R^7$, $-OCOCH_3$, $-OCOCF_3$, $-OCOCH_2NH_2$, $-OPO_3H$, and $-OSO_2CH_3$;

$R^6$ and $R^7$ are independently $-H$, methyl or ethyl;

D is O, N, NH, or N alkyl;

Q is a double bond when D is N and a single bond otherwise;

$R^8$ is H and $R^9$ is H or $R^8$ and $R^9$, together with heteroatom D, the carbon adjacent $R^8$, and the phenyl ring adjacent to $R^9$, form a quinoline ring system (D=N, Q=double bond); and W is —H, —OH, or —$NHR^6$.

In a second form, the new compounds are comprised of a BAPTA-like chelator coupled to two 2-nitrobenzyl derivatives, themselves photochemical precursors of the related 2-nitrosobenzophenones. In this form, the new compounds are comprised of a chemical compound having the generic formula:

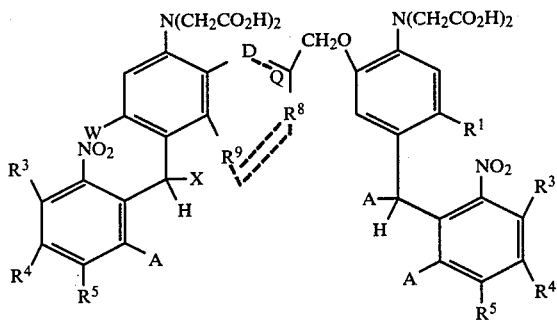

and the pharmaceutically acceptable non-toxic salts and esters thereof wherein:

A is —$NO_2$ or —H;

$R^3$, $R^4$ and $R^5$ are independently —H, OH, $NR^6R^7$, or alkoxy, or $R^3$ and $R^4$ together are —$OCH_2O$— or —$OCH_2CH_2O$— and $R^5$ is —H, OH, $NR^6R^7$, or alkoxy, or $R^4$ and $R^5$ together are —$OCH_2O$— or —$OCH_2CH_2O$— and $R^3$ is —H, OH, $NR^6R^7$, or alkoxy;

X is selected from the group comprised of —OH, alkoxy, 'Cl, —Br, —$NR^6R^7$, —$OCOCH_3$, —$OCOCF_3$, —$OCOCH_2NH_2$, —$OPO_3H$, and —$OSO_2CH_3$;

$R^6$ and $R^7$ are independently —H, methyl or ethyl;

D is O, N, NH, or N alkyl;

Q is a double bond when D is N and a single bond otherwise;

$R^8$ is H and $R^9$ is H or $R^8$ and $R^9$, together with heteroatom D, the carbon adjacent $R^8$, and the phenyl ring adjacent to $R^9$, form a quinoline ring system (D=N, Q=double bond); and W is —H, —OH, or $NHR^6$.

The present invention also comprises a novel method for preparing 1 hydroxy- or 1-alkoxy-1-(2-nitroaryl)-1-aryl methanes. Methanes of this type are either critical to the preparation of, or actually constitute, the photolabile $Ca^{2+}$ chelating compounds disclosed and claimed herein.

According to the disclosed novel method, 1-hydroxy- or 1-alkoxy-1-(2-nitroaryl)-1-aryl methanes having the formula:

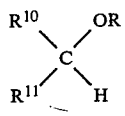

wherein:

R=$C_1$–$C_4$alkyl $R^{10}$=aryl $R^{11}$=2-nitroaryl are prepared by mixing: about one equivalent of an aryl compound which will undergo electrophilic aromatic substitution, about one to two equivalents of a hindered tertiary amine, and about two to four equivalents of TMS triflate; then adding thereto about one to two equivalents of a 1-formyl-2-nitroaryl compound or a dialkoxy acetal thereof; and stirring the reactants until the reaction is complete.

Detailed Description of the Invention

The present invention comprises a new class of calcium chelating compounds which decrease their affinity for calcium when exposed to light. Generic formulas for these photolabile compounds are given above.

Compounds of the type disclosed and claimed herein consist of a $Ca^{2+}$ chelating portion and a nitro aryl portion, connected by a substituted methylene bridge. Examples of these new photolabile compounds include nitr-1, nitr-2, and nitr-3. FIG. 1 outlines the synthetic route utilized in preparing these compounds. Full descriptions of the reaction conditions are described below. In both the figures and the discussion that follows, Roman numerals are sometimes used as a shorthand means of identifying the various chemical compounds.

The present invention relies on the use of a novel method of condensing 2-nitro benzaldehydes or acetals thereof with aryl compounds using trimethylsilyl trifluoromethanesulfonate as a condensing agent. Without the condensing agent, the condensation does not work. A full description of the method is included herein by way of illustration in the synthesis of compounds VII, X, and XIII, infra.

The synthesis of the compounds claimed herein is described in the detailed synthesis of nitr-1 (compound VIII), nitr-2 (compound XI), and nitr-3 (compound XIV), infra. Those skilled in the art will recognize that other new forms of these photolabile $Ca^{2+}$ chelators can be prepared by using related synthetic methods and starting materials.

Preparations of calcium chelating compounds suitable for use as intermediates in this invention have been described (see Tsien, 1980). In addition to the compounds described therein, those skilled in the art will realize that by using standard techniques it is possible to prepare derivatives of said compounds containing various $R^1$, $R^2$, $R^8$, $R^9$, W and D groups (see generic formulas in Brief Description of the Invention section, supra). Such derivatives are within the scope of the present invention. By way of example, the synthesis of 5'-methyl-BAPTA, tetramethyl ester ($R^1$=$R^8$=$R^9$=W=H, $R^2$=$CH_3$, D=O) is illustrated below (compound VIa). This synthesis begins with two substituted 2-nitrophenoxides. One skilled in the art will recognize that other 2-nitrophenoxides with appropriate $R^1$, $R^2$ and W substituents can be used in the same way to prepare other BAPTA derivatives. Briefly, the nitrophenoxides are condensed sequentially with dibromoethane, reduced ($H_2$/Pd), and alkylated with ethyl or methyl bromoacetate.

Other chelating groups within the scope of the invention include derivatives of quinoline ($R^8$ and $R^9$ part of a quinoline ring). Preparation of quinoline analogs of BAPTA has been described (See Tsien, 1980). Similar chelating compounds within the scope of this invention can be prepared using the methods of Tsien (1980) or the teachings of this invention.

The nitrophenyl portion of the new compounds comes from a suitable 2-nitro-benzaldehyde or 2,6-dinitrobenzaldehyde. The aldehyde can be used directly to prepare compounds containing X=OH, or the aldehyde can be modified to an acetal, leading to compounds containing X=Oalkoxy. The advantage of using a nitrobenzaldehyde acetal is that the condensation of such acetals with BAPTA-like aromatic systems proceeds under very mild conditions, using the novel method described below. Acetals are prepared by reacting substituted nitro-benzaldehydes and methoxytrimethylsilane, using TMS-triflate as a catalyst (see Noyori, et al., 1981).

The various R and W substituents allow a number of related compounds to be prepared. When W is —OH, —alkoxy, or —NHR$^6$, the heteroatom may exert electronic and steric effects to modify the stability of the photoactive transition state. R$^1$ and R$^2$ can be altered to modify the $K_d$ of the chelator portion of the molecule, and to control the electrophilic aromatic substitution of the nitrobenzaldehyde derivative so that one or two photolabile groups are incorporated in the final molecule. R$^3$ through R$^5$ substituents will influence the electron density of the nitrophenyl ring and therefore can influence the wavelength needed to activate the photo reaction.

The key step in preparing compounds of the type disclosed and claimed herein is the condensation of a 2-nitrobenzaldehyde, dialkyl acetal, with an aromatic, BAPTA-like chelator. The obvious, textbook methods for synthesizing benzhydrols either failed or were unsuitable because of the many other substituents on the desired molecule. For example, the classic methods for condensing aromatic rings with aldehydes or ketones ("hydroxyalkylation", see March, 1977) are known not to stop at the benzhydrol stage but to go on to triarylmethanes. Also conventional Lewis acids needed to activate the aldehyde would deactivate the BAPTA-like substrates because of their amino functionality. After many failures with the known methods, surprisingly we found that by using the new and unusually selective Lewis acid, trimethylsilyl trifluoromethane sulfonate (see Noyori, et al., 1981), we could carry out the required electrophilic aromatic substitution. No example has heretofore been recorded of the use of TMS-triflate to promote the reaction of aldehydes or acetals to form C—C bonds with aromatic substrates. In previous work (see Noyori, et al., 1981), the substrates were always aliphatic enol silyl ethers, not aromatic compounds. Our new method can be practiced by mixing together one equivalent of an aryl compound and a hindered, tertiary amine, then adding TMS-triflate, and finally adding a 2-nitroaryl aldehyde or dialkyl acetal thereof. By way of example, we have used this method to prepare compounds VII, X and XIII (see synthesis, infra). Thus, compound VII was prepared by mixing 5'-methyl-BAPTA-tetramethyl ester with 2,6-di-tert-butylpyridine and TMS-triflate, then adding 2-nitrobenzaldehyde, dimethylacetal, compound VII, 5-(1-(2-nitrophenyl)-1-methoxymethyl) BAPTA, methyl ester.

In the preparation of compounds of the invention that contain only one photolabile nitrobenzyl group, if R$^2$ is anything except hydrogen, the 5 position of that ring will be blocked and nitrobenzylation can proceed only at the desired 5 position of the 4-W-phenyl ring or equivalent quinoline or benzopyran. If R$^2$ is hydrogen, the presence of halogen at R$^1$ will deactivate that ring for electrophilic substitution and nitrobenzylation will occur mainly at the desired position. Products of the first type where R$^2$=H and R$^1$=H or alkyl can be prepared only by controlled nitrobenzylation and separation of the desired product, so preparation of such compounds is not recommended.

To prepare compounds containing two nitrobenzyl groups, R$^2$ must be hydrogen and R$^1$ can be hydrogen, alkyl or any form appropriate for substituent W. In this case, the desired nitrobenzylation occurs at the 5 position of both phenyl rings or the 5 position of both the R$^1$, R$^2$ phenyl and of the quinoline.

It is known that cation affinities of BAPTA derivatives can be increased or decreased by appropriate electron-donating or electron-withdrawing substituents (see generally Tsien, 1980). For example, substitution of two methyl groups for the two hydrogens para to the two nitrogens of BAPTA strengthened Ca$^{2+}$ binding by 0.4 log unit and similar disubstitution with bromine weakened Ca$^{2+}$ binding by 1.2 log units (see generally, Tsien, 1980). We have found that monosubstitution gives half as much effect on calcium affinity (data not shown). Those skilled in the art will realize that the effect of other substituents on the cation affinities of the present compounds should be quantitatively predictable by a Hammett-type linear free-energy relation.

It is also known that the greatest change in chelating characteristics occurs within 2 log [Ca$^{2+}$] units of the $K_d$ of any particular chelator (see Tsien, 1980). As a result, it would be helpful to have chelators available which have a range of $K_d$'s. To this end, R$^1$ and R$^2$ can be varied to adjust the $K_d$ up or down. As expected, the nitrobenzyl component of the molecule weakens Ca$^{2+}$ binding by 0-0.3 log units (compare $K_d$=160 nM with BAPTA $K_d$=100 nM, (see Tsien, 1980).

Chelators containing W=OH and R$^8$=R$^9$=H are synthesized in seven steps from p-hydroquinone. By way of example, preparation of the BAPTA derivative 1-(2-amino-4-hydroxy-phenoxy)-2-(2'-amino-5'-methylphenoxy)ethane, N,N,N',N'-tetra-acetic acid, tetraethyl ester (XXII) is illustrated below in the synthesis of XXII from hydroquinone, XV. Key steps in the preparation include the acid-catalyzed, selective debenzylation (see Marsh, et. al., 1965) of the phenolic group ortho to the nitro in preference to the phenolic group meta to nitro. The resulting 2-nitro-4 benzyloxyphenol can then be condensed with 2-nitro-4-R$^1$-5-R$^2$-phenoxide and 1,2-dibromoethane, reduced (H$_2$/Pt), and alkylated with ethyl or methyl bromoacetate. Attempts to convert XXI to XXII by hydroxide displacement of benzyloxide were unsuccessful. The remaining benzyl protecting group survives hydrogenation with platinum catalysis (see Freifelder, 1971), but is finally removed by hydrogenation with palladium. Since the 4-benzyloxy substituent will accelerate the rate of nitrobenzylation at the neighboring 5 position, any combination of R$^1$ and R$^2$ can be used in preparing compounds containing one nitrobenzyl group.

The preparation of chelators where W=NHR$^6$ (R$^6$=H, Me, or Et) and R$^8$=R$^9$=H could begin with benzyloxycarbonyl protection of 4-(R$^6$-amino)phenol. Nitration, nitrosation, or coupling with a suitable diazonium salt would yield a substituted phenol analogous to compound XXI, infra. Such a phenol could be condensed with 1-bromo-2-(2-nitro-4-R$^1$-5-R$^2$-phenoxy)ethane, and reduced (H$_2$/Pt). Any of nitro, nitroso or azo groups will thereby be reduced to NH$_2$ without affecting the benzyloxycarbonyl groups. After alkylation with alkyl bromoacetate, the benzyloxycarbonyl group would be removed by hydrogenation with palladium on carbon to give an chelator with W=NHR$^6$.

The preparation of chelators in which $R^8$ and $R^9$ are part of a quinoline ring, has been described (see Tsien, 1980). Starting with, for example, 2-methyl-6-W-8-nitroquinoline, the 2-methyl group is iodinated to iodomethyl, then condensed with potassium 2-nitro-4-$R^1$-5-$R^2$-nitrophenoxide. The product is then reduced (Pt/H$_2$), and alkylated with methyl or ethyl bromoacetate (see Tsien, 1980) to give the desired chelator. One skilled in the art can use these teachings to prepare other compounds containing various groups $R^1$, $R^2$, $R^8$, and $R^9$.

The preparation of chelators where $R^8$ and $R^9$ are part of a quinoline ring and W=OH begins, for example, with 2-methyl-6-methoxy-8-nitroquinoline. The methoxy group could be cleaved with BBr$_3$ or hot HI to yield a 6-hydroxy group, which could then be protected by reaction with dimethoxymethane under acid catalysis to yield 2-methyl-6-methoxymethyloxy-8-nitroquinoline. This can be used as starting material for the synthesis outlined above for 2-methyl-6-W-8-nitroquinoline, leading to chelators with W=OCH$_2$OCH$_3$. Mild acid hydrolysis of this compound gives chelators with W=OH.

Chelators where $R^8$ and $R^9$ are part of a quinoline ring and W=NHR$^6$ could be prepared, for example, from 2-methyl-6-(R$^6$-amino)-8-nitroquinoline by protecting the amine as benzyloxycarbonyl, then iodinating, condensing with 2-nitro-4-$R^1$-5-$R^2$-nitrophenoxide, reducing, and alkylating with alkylbromoacetate (see Tsien, 1980). Hydrogenation of such a compound with palladium on carbon gives chelators with W=NHR$^6$.

The photolabile compounds disclosed and claimed herein could also be esterified using an alpha-alkyloxyalkyl bromide. Such esters are hydrophobic enough to readily cross cell membranes, but once within the cell are cleaved by cytosolic esterases to regenerate the free acids. By way of example, acetoxymethyl esters of the photolabile compounds discussed and claimed herein can me made by : saponifying the methyl or ethyl esters of the target chelator (for example, compounds IX, XII, XVI, XXVIII, XXXI, or XXXIV, below and in FIG. 1) with KOH, adding four to six equivalents of a tetrabutylammonium salt (preferably the hydroxide), and evaporating in vacuo to dryness. The residue was then extracted with dichloromethane, which dissolved the dyes as the tetrabutylammonium salts. This organic solution was dried thoroughly in vacuo, and the residue was taken up in dichloromethane, mixed with about 5-10 equivalents (per dye) of acetoxymethyl bromide (prepared according to the new method disclosed herein, see Acetoxymethyl Bromide, described infra in Compound Synthesis) and about 2 equivalents (per dye) of ethyl diisopropylamine, then stirred overnight. The solvent was then evaporated, the residue was taken up in benzene or toluene, washed with aqueous bicarbonate and water, dried and evaporated. The products were generally pure enough for use, but could be further purified on silica gel, if necessary.

Figure 2:
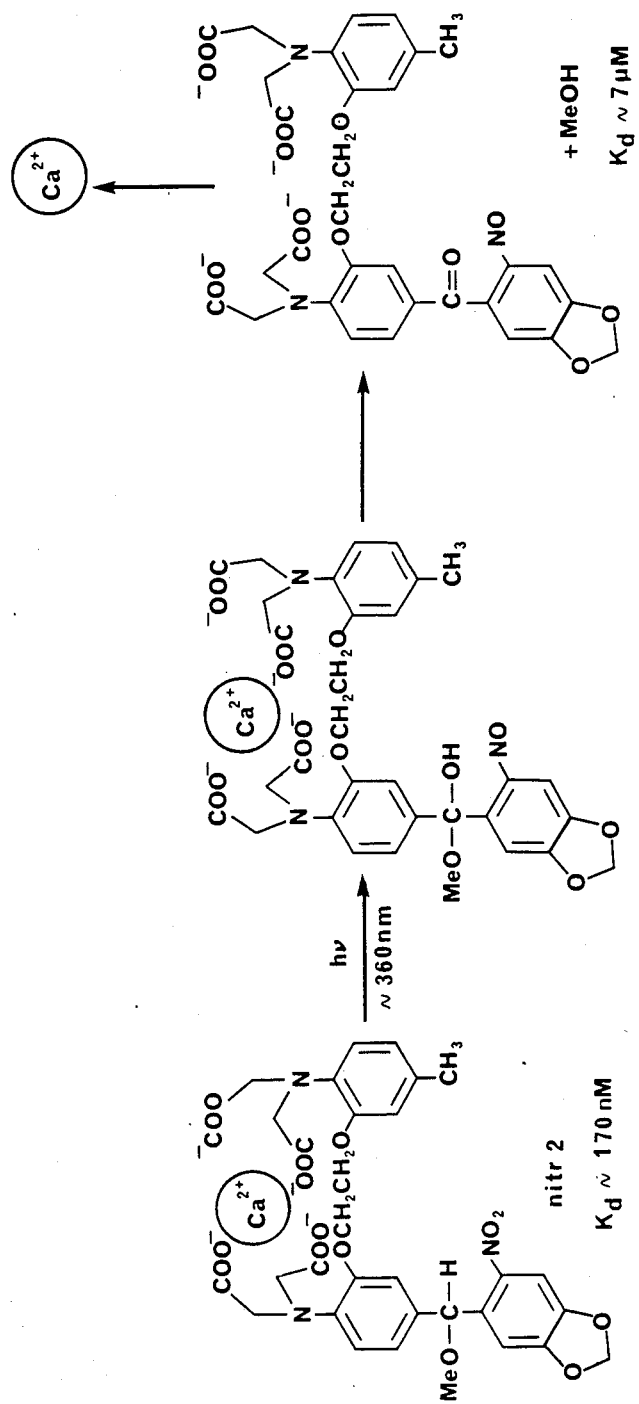
FIG. 2 is a chemical flow chart illustrating the photolysis of the $Ca^{2+}$-complex of nitr-2.

Methods for synthesizing the new photolabile Ca$^{2+}$ chelators disclosed herein are outlined in the Compound Synthesis section infra. Specific properties and embodiments of the new chelators, as exemplified by the compounds nitr-1, nitr-2, and nitr-3, are discussed in Examples I and II, and the Figures referred to therein. Example I discloses and discusses in vitro chemical tests using nitr-1 and nitr-2. Results of those tests are illustrated in FIGS. 3-6. Example II discloses and discusses biological testing of nitr-2. Results of those tests are illustrated in FIGS. 7 and 8. Each will be discussed separately below. As background FIG. 2 is useful since it outlines the photolysis mechanism at the molecular level.

Figure 3:
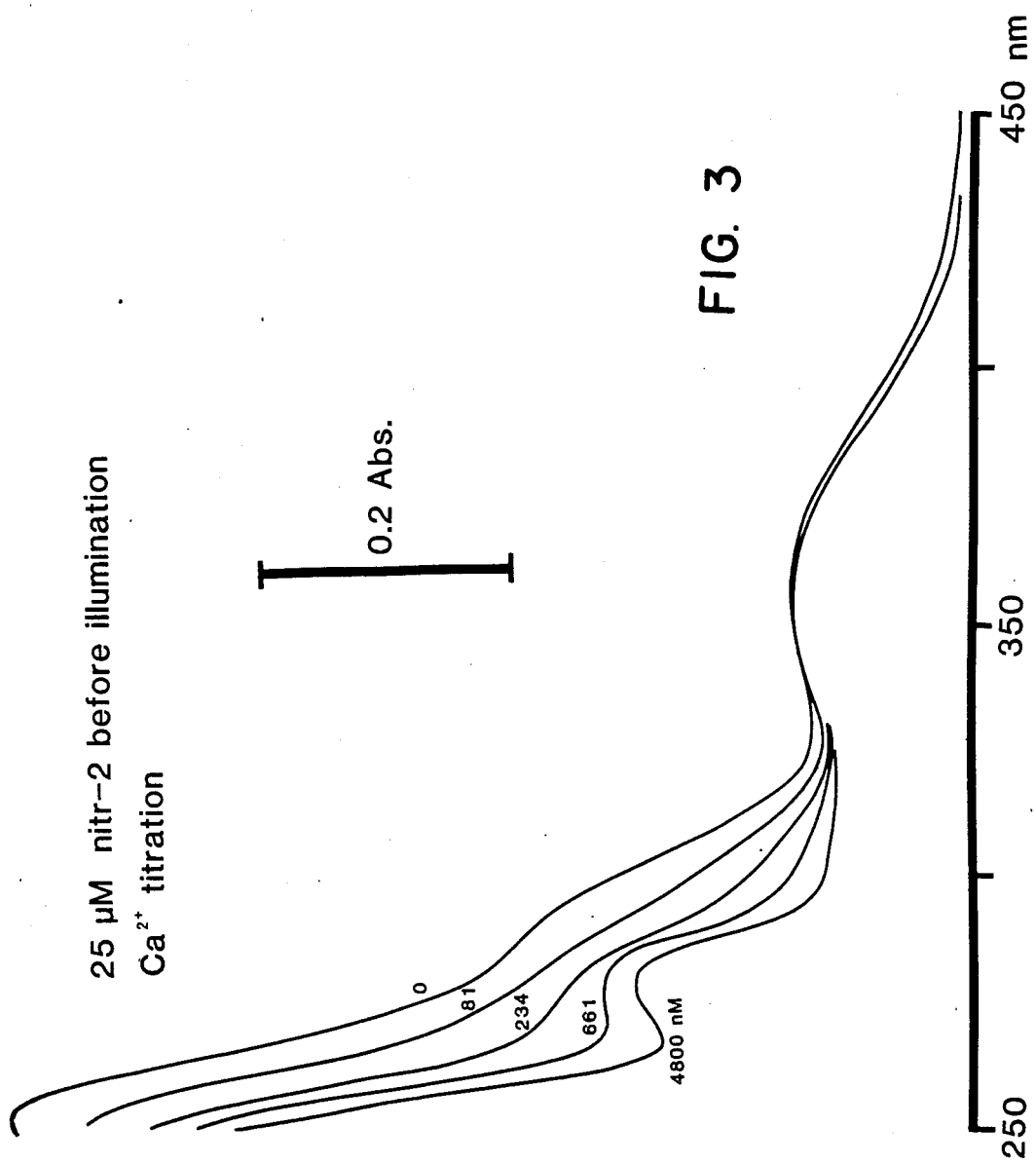
FIG. 3 is a graph showing absorption spectra for nitr-2, before illumination, at various $Ca^{2+}$ concentrations.

FIG. 3 shows that before photolysis, nitr-2 has a high affinity for Ca$^{2+}$. In determining this 25 microM nitr-2 was dissolved in 100 mM KCl, 4 mM dipotassium salt of N-(hydroxyethyl)-ethylenediamine-N,N',N'-triacetic acid (HEEDTA), 10 mM tris (hydroxymethyl)aminomethane, 2 mM MOPS, pH 8.84. The absorbance spectrum was then recorded giving the curve labeled "0". Then 2 mM CaCl$_2$ was added as well as enough concentrated KOH to raise the pH to 9.14. At this pH the calculated free [Ca$^{2+}$] in the buffer was 41 nM. The spectrum was recorded again. Successive additions of HCl lowered pH to 8.81 (free Ca$^{2+}$ 81 nM), 8.57 (free Ca$^{2+}$ 135 nM), 8.33 (free Ca$^{2+}$ 234 nM), 8.10 (free Ca$^{2+}$ 398 nM), 7.88 (free Ca$^{2+}$ 661 nM), 7.50 (free Ca$^{2+}$ 1.585 microM), and 7.03 (free Ca$^{2+}$ 4.79 microM). Though absorption spectra were recorded at each pH, for clarity only every other curve has been reproduced in this figure, each being labeled by the free Ca$^{2+}$ in units of nM. Addition of 3 mM extra CaCl$_2$ at the end, to raise free Ca$^{2+}$ to 1 mM, produced no further spectral change, confirming that 4.79 microM free Ca$^{2+}$ was already saturating. Analysis of all the absorption at 266 nm by the usual Hill plot showed that the dissociation constant was 160 nM. The method used here for manipulating free Ca$^{2+}$ relies on the known facts that BAPTA derivatives are practically insensitive to pH as such above pH 6.5, whereas the Ca$^{2+}$ affinity of HEEDTA is strongly dependent on pH in a known way. All manipulations were performed under orange safelight illumination to avoid photolysis.

Figure 4:
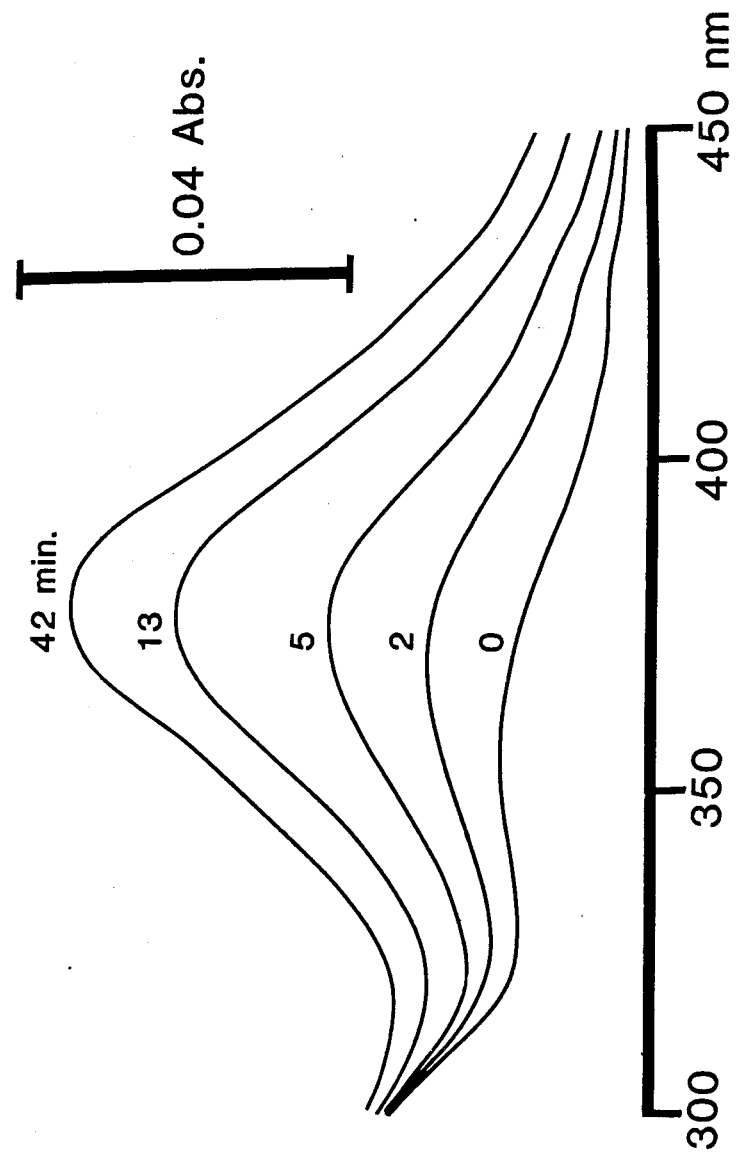
FIG. 4 is a graph showing absorption spectra for nitr-2, illuminated at 365 nm, in the absence of $Ca^{2+}$.

FIG. 4 characterizes the photoisomerization of nitr-2 in the absence of Ca$^{2+}$. It shows representative absorption spectra for a sample of 4 microM nitr-2 dissolved in calcium-free aqueous solution containing 130 mM KCl, 1 mM EGTA, 10 mM MOPS, brought to pH 7.2 with KOH. The curve labeled "0" was measured before any exposure of the sample to significant levels of ultraviolet radiation. (Control experiments showed that the Cary 210 spectrophotometer used negligible intensity of UV to measure these spectra). The curves labeled "2", "5", "13" and "42 min" show the successive spectra remeasured after those durations of cumulative exposure to 365 nm irradiation from an Ultraviolet Products Inc. UVGL-58 lamp at a distance of 1 cm. The intensity at this position had been separately measured to be $7.8 \times 10^{-9}$ einsteins · cm$^{-2}$ · sec$^{-1}$. Spectra were also measured at times of 1, 3, 8, 20, and 30 minutes but are omitted here merely for graphical clarity; they do confirm that the "42 min" curve represents >99% completion of the photochemical change. Solutions were at room temperature and continually stirred by a magnetic follower during illumination. At these low light levels, the conversion of nitr-2 in to its isomeric nitrosobenzophenone is entirely rate-limited by the ability of nitr-2 to catch photons, not by the subsequent dark reactons such as collapse of the hemiketal. Because the total optical density remained low throughout, the optical density was expected (see Brown, 1971) and found to approach its asymptotic value in an exponential manner. The quantum efficiency is known (see Brown, 1971) to be given by the reciprocal of the product of the time in seconds to reach 90% conversion, the incident light intensity in einsteins · cm$^{-2}$ · sec$^{-1}$ and the extinction coefficient in cm$^2$·mole$^{-1}$. In this experiment the quantum efficiency was found to be 0.03.

Figure 5:
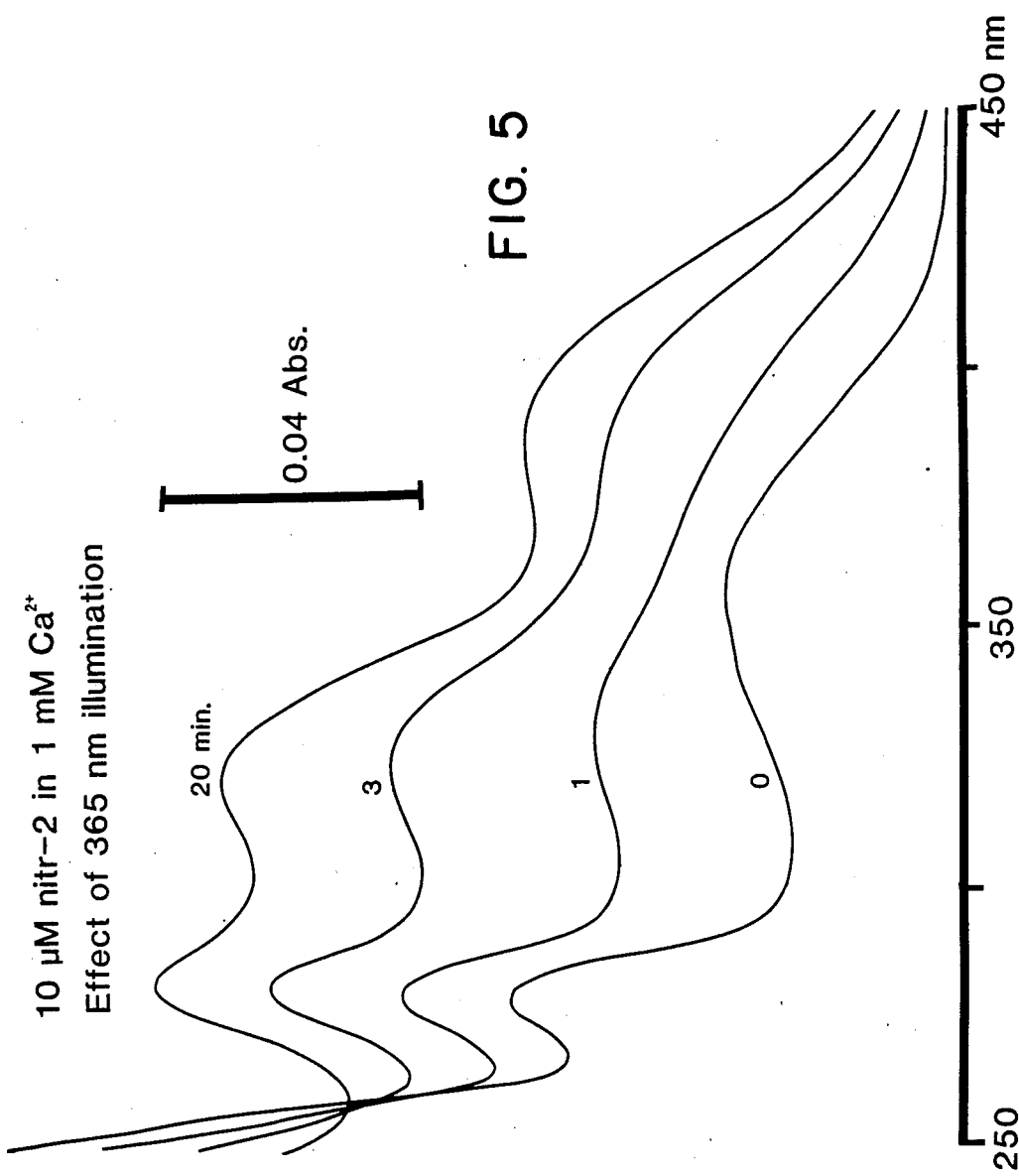
FIG. 5 is a graph showing absorption spectra from $Ca^{2+}$-complexes of nitr-2 illuminated at 365 nm for varying lengths of time.

FIG. 5 characterizes the photoisomerization of the Ca$^{2+}$-complex of nitr-2. It shows absorption spectra for 10 microM nitr-2 dissolved in 130 mM KCl, 1 mM CaCl$_2$, 10 mM MOPS, pH titrated to 7.2 with KOH. Spectra were obtained after 0, 20 sec, 1 min, 2, 3, 5, 8, 13, and 20 min of 365 nm illumination, exactly as in FIG. 4. Again for clarity, only the 0, 1, 3, and 20 minute spectra have been reproduced here. The 13 minute and 20 minute spectra were identical, confirming completion of photolysis after those times. It is obvious that photoisomerization approaches completion more rapidly here in high [Ca$^{2+}$] than in zero [Ca$^{2+}$] (FIG. 4). The quantum efficiency was determined to be 0.1 for the conversion of Ca$^{2+}$-nitr-2 to the Ca$^{2+}$-nitrosobenzophenone studied here.

Figure 6:
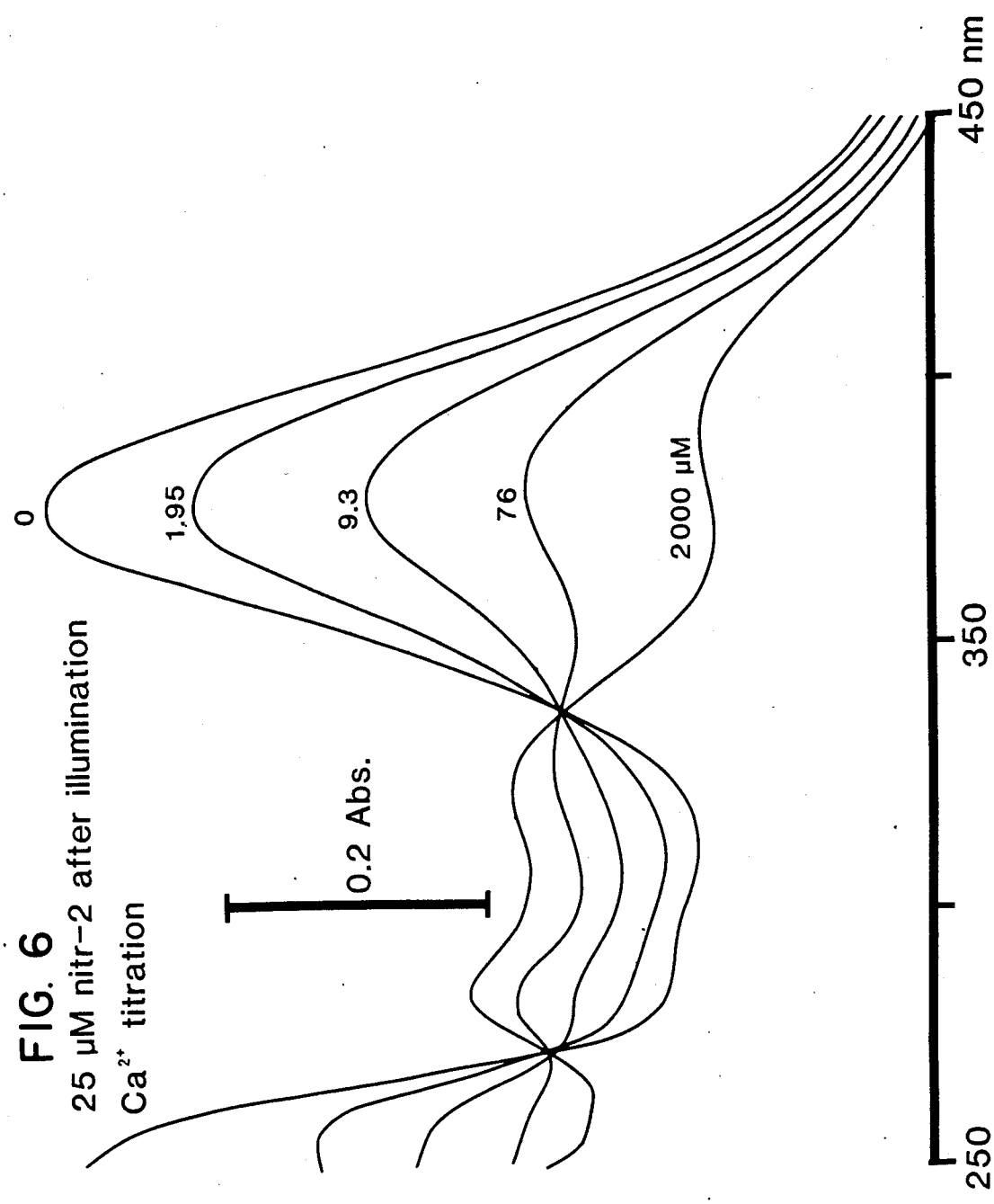
FIG. 6 is a graph showing absorption spectra from the nitrosobenzophenone photolysis product at various $Ca^{2+}$ concentrations.
Figure 7:
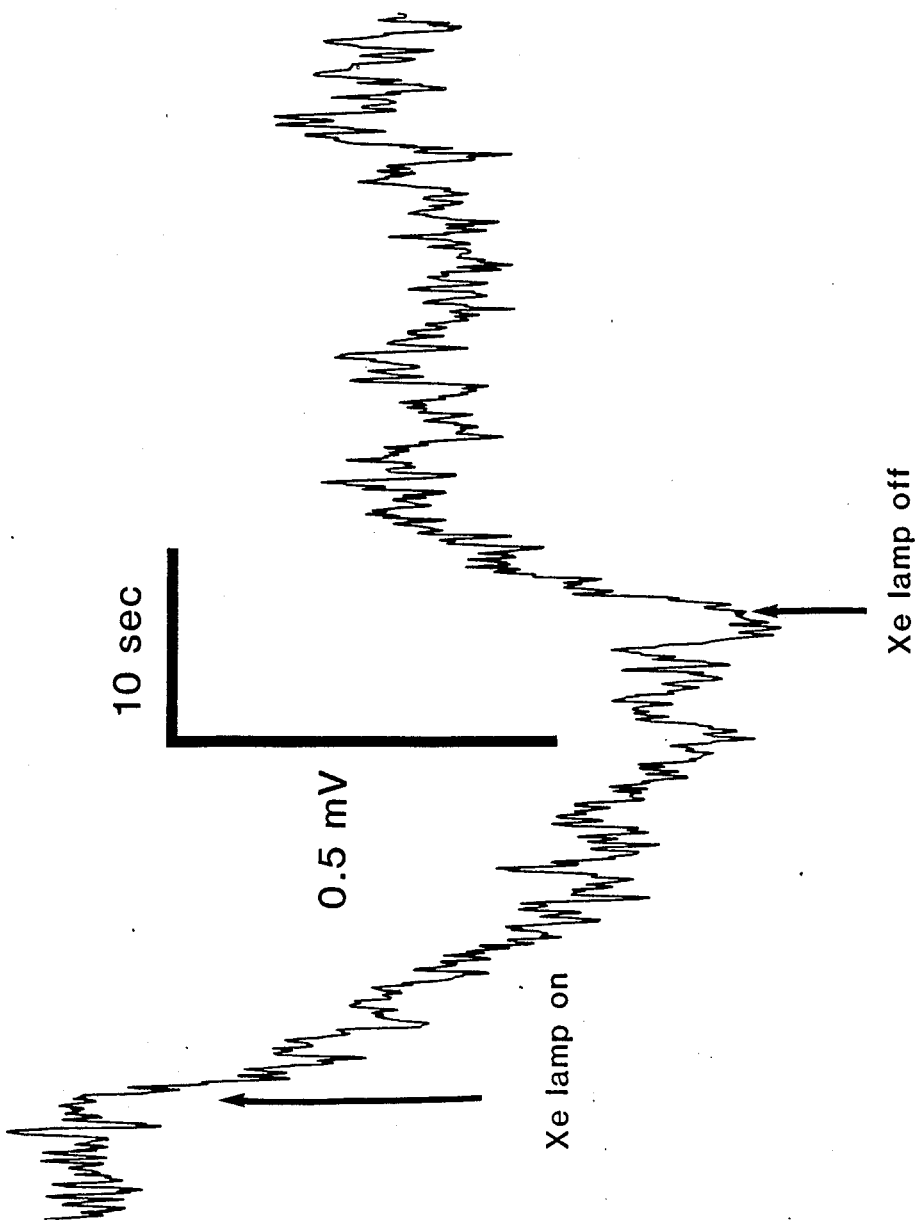
FIG. 7 is a time-voltage plot illustrating that a neuron injected with nitr-2 slightly hyperpolarizes on illumination.

FIG. 6 shows that the nitrosobenzophenone photolysis product has a low affinity for Ca$^{2+}$. The nitrosobenzophenone was produced by dissolving 25 microM nitr-2 in 100 mM KCl, 2 mM CaCl$_2$, 10 mM tris(hydroxymethyl)aminomethane, 2 mM MOPS, pH 8.8, and irradiating for ~20 min with the UVGL-58 lamp at 365 nm to complete the photolysis. The spectrum labeled 2000 microM was then recorded. 4 mM dipotassium salt of HEEDTA was then added, plus enough KOH to raise the pH to 10.3 (free Ca$^{2+}$ <10$^{-8}$ M), whereupon the spectrum labeled "0" was recorded. Then HCl was added in analogy to FIG. 3, to reach the following pH and free Ca$^{2+}$ values in parentheses: 8.53 (0.117 microM), 8.13 (0.372 microM), 7.82 (0.759 microM), 7.41 (1.95 microM), 7.05 (4.57 microM), 6.77 (9.33 microM), 6.35 (26.3 microM), 5.93 (75.8 microM). The only intermediate spectra shown in this figure correspond to the underlined values. The usual Hill plot showed a dissociation constant in the range 7–10 microM.

FIG. 7 shows that illumination of nitr-2 can raise the free [Ca$^{2+}$] level inside a live nerve cell. A particular neuron, conventionally designated L2, in the abdominal ganglion of the sea hare *Aplysia californica*, received a microinjection of nitr-2 solution amounting to approximately 2% of the cell's volume. This nitr-2 solution contained 400 mM nitr-2 tetraanion, 300 mM Ca$^{2+}$ with the ionic balance made up with K$^+$. The cell therefore received about 8 mM nitr-2 and 6 mM Ca$^{2+}$. It was also impaled with a separate microelectrode to record its membrane potential. At the time marked by the first arrow, a shutter was opened permitting a 75 watt xenon arc lamp to illuminate the cell through a quartz focusing lens. The membrane potential went more negative (hyperpolarized) as expected for a rise in [Ca$^{2+}$]$_i$ which would open a Ca$^{2+}$-activated potassium conductance in the membrane. The effect partly reversed when the light was blocked (see second arrow). Development of this potassium conductance is one of the best-understood consequences of elevating [Ca$^{2+}$]$_i$ in this cell type.

There are at least four reasons why the hyperpolarizing effect was small: (1) Nitr-2 is still far from ideal in extinction coefficient and quantum efficiency. (2) The xenon lamp intensity could be increased. (3) The particular cell used contains a large amount of natural yellow pigment that absorbs UV light. Therefore only the small fraction of the cell volume most directly facing the lens was effectively irradiated. (4) The high ionic strength (300–500 mM) present inside a marine invertebrate like Aplysia further weakens the binding of Ca$^{2+}$ to unphotolyzed nitr-2. The lower the fraction of nitr-2 molecules bearing Ca$^{2+}$ before photolysis, the fewer Ca$^{2+}$ ions there are to be released by light, and the less the quantum efficiency of isomerization of nitr-2 to the nitrosobenzophenone. Nitr-2 would be expected to be much more effective in any vertebrate cell, since vertebrates have much lower ionic strengths (~150 mM).

FIG. 8 shows an experiment identical to FIG. 7 except that the cell's electrophysiological response was measured differently. Here the cell was maintained under voltage clamp, a setup by which an electronic feedback amplifier injects into the cell whatever current is necessary to maintain the membrane potential at a constant value, chosen here to be −35 mV. Before the nitr-2 was introduced, illumination had no effect on the current required (see trace marked uninjected control). After the nitr-2 was injected as in FIG. 7, illumination causes the cell membrane to conduct more current outwards. An equal current is injected by the feedback amplifier in order to hold the membrane potential constant. An increased outward current is another manifestation of a Ca$^{2+}$-activated potassium conductance.

Compound Synthesis

Most reagents and solvents used in the syntheses were ACS or HPLC grade, and used as received from Aldrich, Mallinkradt, Fisher, or J. T. Baker. Dry dimethylformamide and dry pyridine were obtained from Aldrich, Gold Label, stored over 4A molecular sieves and used as received. Potassium salts of 2-nitrophenoxides were prepared by adding a stoichiometric amount of concentrated aqueous KOH to the nitrophenol in methanol, then evaporating the solvent in vacuo until the stoichiometric weight was reached.

In testing the various reaction products, proton NMR spectra were recorded on Varian instruments at 60 MHz (EM-360), 80 MHz (CFT-20), 90 MHz (EM-390), and 100 MHz (HA-100). Peaks are reported below in the following format: NMR (solvent, operating frequency): chemical shift in ppm from tetramethylsilane, multiplicity (s=singlet, d=doublet, t=triplet, q=quartet, m=multiplet, br=broad), spin-spin coupling constant if appropriate, integrated number of protons. Sometimes several adjacent peaks are too close for their integrals to be separated, in which case only the total integral for a cluster is stated.

Referring now to the generic formulas shown in the Brief Description of the Invention section, supra, and in the claims infra, to prepare compounds with X=OH, the esters with X=OMe could be demethylated with standard reagents such as boron tribromide or trimethylsilyl iodide. Although all ester groups in the compound may be cleaved and R$^3$, R$^4$, and R$^5$ may be dealkylated as well under such conditions, R$^3$, R$^4$, and R$^5$ can be restored to their original state of alkylation by using a suitable diazoalkane or by alkylation with the appropriate alkyl halide in the presence of a weak base such as a hindered tertiary amine or potassium carbonate. These bases are not strong enough to realkylate the benzylic alcohol group, X=OH.

An alternative preparation of the compounds with X=OH would be to use the parent aldehydes in place of the dimethyl acetals used in the synthesis examples described below, as electrophiles toward BAPTA-like esters VIa or VIb (see synthesis, infra). Using more vigorous conditions such as refluxing in chloroform for several days, the reaction of ester VI with 2-nitro-aldehydes in the presence of TMS-triflate and a hindered tertiary amine should give the compounds claimed herein, with X=OSi(CH$_3$)$_3$, which will hydrolyze spontaneously to X=OH upon aqueous workup.

Those skilled in the art will realize that starting from esters where X=OH, analogs containing X=—O—acetyl,—OCOCF$_3$, —O—glycyl, —OPO$_3$H, —OSO$_2$CH$_3$ could be readily prepared by acylation, phosphorylation, or methanesulfonylation under standard conditions. Also starting from esters where X=OH, analogs with X=—Cl or —Br could be prepared using SOCl$_2$ or PCl$_3$ or PBr$_3$ or other standard means for converting alcohols to halides. Esters with X=NR$^6$R$^7$ could be prepared from esters with X=Br or X=OSO$_2$CH$_3$ by nucleophilic substitution under standard conditions.

COMPOUND II 1-bromo-2-(2'-nitro-5'-methylphenoxy)ethane (II) was prepared as follows:

57.6 g (0.30 mole) potassium 2-nitro-5-methylphenoxide (I), 187.4 g (1.0 mole) 1,2-dibromoethane, and 151 g dimethylformamide were heated together to 120°. The bright orange color of the reaction mixture soon faded to pale yellow and a white precipitate was deposited. After cooling, the precipitate was filtered off and washed with water and dichloromethane. The insoluble residue was 1,2-bis(2-nitro-5-methylphenoxy)ethane, 5.87 g (0.018 mole). The combined organic phases of the filtrate were washed repeatedly with dilute NaOH until no more orange color appeared in the extracts, then washed once with saturated aqueous NaCl containing a little NaH$_2$PO$_4$. After drying over MgSO$_4$, the organic phase was evaporated to dryness and the residue recrystallized either from petroleum ether (b.p. 60°–80°) or methanol-water. The yield of II was 34 g (44%), m.p. 44°14 45°. NMR (CDCl$_3$, 60 MHz): 7.75, d, 8Hz, 1H; 6.9–6.75, m, 2H; 4.36, t, 7 Hz, 2H; 3.6, t, 7 Hz, 2H; 2.36, s, 3H.

COMPOUND IV 1-(2-nitrophenoxy)-2-(2'-nitro-5'-methylphenoxy)ethane (IV) was prepared as follows:

5.32 g (20.5 mmole) II and 3.98 g (22.5 mmole) potassium 2-nitrophenoxide (III) were stirred in 10 ml dimethylformamide and heated to 130° for 80 min. The mixture was cooled, diluted to 100 ml with water, and filtered; the precipitate was washed repeatedly with aqueous Na$_2$CO$_3$ and then water. After drying, it was recrystallized from 1.25 l boiling 95% ethanol containing 5 ml acetic acid, to which a little water was added after cooling. The yield of IV was 5.55 g, 85%, m.p. 150°–152°. NMR (CDCl$_3$, 60 MHz): 7.7–6.6, m, 7H; 4.34, s, 4H; 2.26, s, 3H.

COMPOUND V 1-(2-aminophenoxy)-2-(2'-amino-5'-methylphenoxy)ethane (V) was prepared as follows:

5.55 g IV were hydrogenated at room temperature and atmospheric pressure with 0.46 g palladium (5% on charcoal) catalyst in 95% ethanol. After full hydrogen uptake (13 hrs), the mixture was warmed, filtered while hot, decolorized with a pinch of NaBH$_4$, and chilled to −10°; the yield of V as white crystals was 4.03 g, 89%, m.p. 118°–119°. NMR (CDCl$_3$, 80 MHz): 6.8–6.5, m, 7H; 4.28, s, 4H; 3.5–3.7, br s, 4H; 2.24, s, 3H.

COMPOUNDS VIa and VIb 1-(2-aminophenoxy)-2-(2'-amino-5'-methylphenoxy)ethane-N,N,N',N'-tetraacetic acid, tetraethyl ester (VIa) or tetramethyl ester (VIb) were prepared by either of two methods, as follows:

2.58 g (10 mM) V, 11.3 g (53 mM) 1,8-bis(dimethylamino)naphthalene, 0.79 g (5.3 mM) sodium iodide, 8.91 g (53 mM) ethyl bromoacetate, and 9.5 g acetonitrile were stirred and refluxed under nitrogen for 18 hrs. The cooled mixture was diluted with toluene and filtered. The filtrate was extracted with phosphate buffer at pH 2 until the 1,8-bis(dimethylamino)naphthalene was removed. The toluene solution was dried and evaporated and the residue recrystallized from 50 ml ethanol. The yield of the tetraethyl ester, VIa, was 5.27 g, 87%, m.p. 110°–110.5°. NMR (CDCl$_3$, 100 MHz): 6.88–6.6, m, 7H; 4.30, s, 4H; overlapping 4.18, s, 4.14, s, 4.08, q, 7 Hz, total 16H; 2.28, s, 3H; 1.18, t, 7 Hz, 12H.

In a larger-scale repetition, ethyl bromoacetate was replaced by methyl bromoacetate and 1,8-bis(dimethylamino)naphthalene was replaced by Na$_2$HPO$_4$, dried at 150°. Thus 25.83 g (100 mM) V, 71 g (500 mM) dried Na$_2$HPO$_4$, 5.9 g (39 mM) NaI, 84.7 g (554 mM) BrCH$_2$CO$_2$Me and 104 g CH$_3$CN refluxed under nitrogen with vigorous stirring by a crescent-shaped paddle for 18 hrs. The cooled reaction mixture was partitioned between water and toluene. The organic phase was evaporated to dryness and recrystallized from methanol. The yield of the tetramethyl ester, VIb, was 40.2 g (71%). After another crystallization from methanol, the m.p. was 95°–95.50°. NMR (CDCl$_3$, 90 MHz): 6.83, s, 6.67, m, total 7H; 4.24, s, 4.13, s, 4.09, s, total 12H; 3.56, s, 3.54, s, total 12H; 2.23, s, 3H.

COMPOUND VII 1-(2-amino-5-(1-methoxy-1-(2-nitrophenyl) methyl)-phenoxy)-2-(2'-amino-5'-methylphenoxy)-ethane-N,N,N',N'-tetraacetic acid, tetramethyl ester (VII) was prepared as follows:

0.2 mmole VIb, 200 mg 2-nitrobenzaldehyde dimethyl acetal (prepared from 2-nitrobenzaldehyde by standard means, i.e., transacetalization with trimethyl orthoformate), 4 ml CH$_2$Cl$_2$, 0.2 ml trimethylsilyl trifluoromethanesulfonate, and 0.2 ml 2,6-di tertbutylpyridine were combined and left at room temperature for 24 hrs. The organic phase was equilibrated with aqueous NaHCO$_3$, dried over MgSO$_4$, evaporated to dryness, and chromatographed on silica with toluene-ethyl acetate 4:1 v/v as eluant. The product with higher R$_F$ and a tendency to turn yellow upon UV illumination was collected. NMR (CCl$_3$, 90 MHz): 7.9–7.1, m, 4–5H; 6.9–6.5, m, 6–7 H; 5.83, s, 1H; 4.3–4.0, m, 12–14 H; 3.55, s, 3.50, s, total 12–14H; 3.28, s, 3H; 2.20, s, 3H.

COMPOUND VIII 1-(2-amino-5-(1-methoxy-1-(2-nitrophenyl) methyl)-phenoxy)-2-(2'-amino-5'-methylphenoxy)- ethane-N,N,N',N'-tetraacetic acid (VIII) was prepared as follows:

VII was saponified by dissolving 43 mg (70 micromoles) VII in a mixture of 0.5 ml dioxane, 1.0 ml methanol, and 0.4 ml 1N NaOH. This mixture was left in darkness overnight.

COMPOUND IX 2-nitro-4,5-methylenedioxybenzaldehyde, dimethyl acetal (IX) was obtained by reaction of 6-nitropiperonal with excess methoxytrimethysilane in the presence of trimethylsilyl trifluoromethanesulfonate in CH$_2$Cl$_2$ at −78° C., according to the general procedure of Noyori, (1982).

COMPOUND X 1-(2-amino-5-(1-methoxy-1-(2-nitro-4,5-methylenedioxyphenyl)methyl)phenoxy)-2-(2'-amino-5'-methylphenoxy)ethane-N,N,N',N'-tetraacetic acid, tetraethyl ester (X) was prepared as follows:

602 mg (1 mmol) VIa and 0.4 ml 2,6-di-t-butylpyridine (0.4 ml) were dissolved in 10 ml of dry dichloromethane, with stirring, under nitrogen and cooled to 0°. To this mixture was added 0.3 ml trimethylsilyltrifluoromethanesulfonate in one portion. After 10 minutes, 0.4 g of 2-nitro-4,5-methylenedioxybenzaldehyde, dimethyl acetyl, IX (dissolved in 5 ml dry $CH_2Cl_2$) was added dropwise from a syringe over 40 min. From this point onward, the materials were protected from short-wavelength light as much as possible by wrapping the reaction vessels in aluminum foil and working under a yellow safelight. The reaction was stirred at 0° for three hours more, then diluted with dichloromethane and washed with aqueous $NaHCO_3$. The organic layer was dried with anhydrous sodium sulfate in darkness, filtered, and evaporated. The syrupy residue was chromatographed on silica gel, eluting with toluene-ethyl acetate 4:1 (v/v). The yield was 0.598 g, 74%, of a thick syrup, pure by TLC and by NMR (trace of toluene). NMR ($CDCl_3$, 90 MHz): 7.3–7.1, m; 6.9–6.6, m; 6.0, s; 5.88, s; 4.3–3.9, m; 3.29, s; 2.20, s; 1.12, t, 7 Hz.

COMPOUND XI 1-(2-amino-5-(1-methoxy-1-(2-nitro-4,5-methylenedioxyphenyl)methyl)phenoxy)-2-(2'-amino-5'-methylphenoxy)ethane-N,N,N',N'-tetraacetic acid (XI).

Ester X was saponified by dissolving 78 mg (0.096 mmole) X in 2 ml dioxane, 1 ml methanol, and 0.8 ml 1N NaOH, and leaving this mixture overnight at room temperature, protected from light.

COMPOUND XII 2,6-dinitro-3-methoxybenzaldehyde, dimethyl acetal (XII) was prepared by the same method used for making compound IX but using 2,6-dinitro-3-methoxybenzaldehyde, for a starting material and reacting overnight at room temperature instead of −78°. After washing with aqueous $NaHCO_3$, drying, and evaporating the solvent, the product was pure by TLC and NMR.

COMPOUND XIII 1-(2-amino-5-(1-methoxy-1-(2,6-dinitro-3-methoxyphenyl)methyl)phenoxy)-2-(2'-amino-5'-methylphenoxy)ethane-N,N,N',N'-tetraacetic acid, tetramethyl ester (XIII) was prepared as by the same method used to make compound X, except starting with VIb instead of VIa and XII in place of IX and stirring overnight at room temperature instead of three hours at 0°. The product was purified by preparative thin layer chromatography on silica gel plates, eluting with hexane-ethyl acetate 1:1. NMR ($CDCl_3$, 90 MHz): 7.85, d, 9 Hz, 1H; 6.95, d, 9 Hz, 1H; 6.85–6.45, m, 6H; 5.86, s, 1H; 4.12, s, 4H; 4.02, s, 3.98, s, total 8H; 3.85, s, 3H; 3.43, s, 3.41, s, total 12H; 3.22, s, 3H, 2.14, s, 3H.

COMPOUND XIV 1-(2-amino-5-(1-methoxy-1-(2,6-dinitro-3-methoxyphenyl)methyl) phenoxy)-2-(2'-amino-5'-methylphenoxy)ethane-N,N,N',N'-tetraacetic acid (XIV) was prepared as follows:

20 micromoles of XIII was saponified in a mixture of 0.6 ml dioxane, 0.2 ml methanol, and 0.2 ml 1M KOH, standing overnight at room temperature, protected from light.

COMPOUND XVI 1,4-di(benzyloxy)benzene (XVI) was prepared as follows:

To a stirred suspension of 55 g (0.5 mole) hydroquinone (XV) and 143.1 g (1.1 mole) benzyl chloride in 100 ml ethanol was added a solution of 60.2 g (0.91 mole) potassium hydroxide in ethanol. After 1 hr, the mixture was poured into water. The precipitate was filtered off several hours later, dried at 70°, and recrystallized from 3.5 liters of boiling ethanol. The yield of XIX was 105 g, 73%, m.p. 128°–130° (literature values (32) range from 126.5 to 130°). NMR ($CDCl_3$, 100 MHz): 7.35, s, 10H; 6.87, s, 4H; 4.98, s, 4H.

COMPOUND XVII 2-nitro-1,4-di(benzyloxy)benzene (XVII) was prepared as follows:

18 3 g (0.203 mole) 70% aqueous nitric acid were diluted to 50 ml with glacial acetic acid and added to a suspension of 58 g (0.200 mole) XVI in 200 ml acetic acid. The mixture was stirred and gently warmed to 50°, whereupon the starting material dissolved and product began to crystallize out. After cooling the mixture and filtering off a first crop, water was added dropwise to precipitate a second crop. The total yield of XVII was 65.6 g, 98%, m.p. 81°–82.5° (83° was reported in ref. 33). NMR ($CDCl_3$, 100 MHz): 7.5–6.9, M, 13H; 5.15, s, 5.03, s, total 4H.

COMPOUND XVIII 2-nitro-4-benzyloxyphenol (XVIII) was prepared as follows:

A solution of 50.4 g (0.15 mole) XVII in 100 ml ethanol-free chloroform was treated with 15.0 ml (0.2 mole) trifluoroacetic acid and kept at room temperature for 48 hours, at which time an NMR spectrum showed ca. 90% conversion of the starting material, as judged by the amplitude of the peak at=4.92. The excess acid was neutralized with 5M aqueous potassium hydroxide. The organic phase was repeatedly extracted with dilute aqueous potassium carbonate until the aqueous layer was pale orange instead of dark brown as at first. The chloroform solution was then diluted with 1.5 volumes of diethyl ether and treated with 60 ml 5M potassium hydroxide. The dark red precipitate of potassium 4-benzyloxy-2-nitrophenoxide was filtered off, acidified with dilute HCl, and extracted with six 600 ml portions of petroleum ether (b.p. 60°–80°). After combining the extracts and evaporating the petroleum ether, the residue was recrystallized from boiling methanol to which water was added dropwise after cooling. The yield of XVIII was 31–32 g, 84–87%, m.p. 67°–70°.

NMR ($CCl_4$, 100 MHz): 10.24, s, 1H; 7.52, d, 3 Hz, 1H; 7.32, s, 5H; 7.19, dd, 3 Hz, and 9 Hz, 1H; 7.00, d, J=9 Hz, 1H; 5.01, s, 2H.

COMPOUND XIX 1-(2-nitro-4-benzyloxyphenoxy)-2-(2'-nitro-5'-methylphenoxy)ethane (XIX) was prepared as follows:

A mixture of 2.45 g (10 mmole) XVIII, 2.8 g (108 mmole) II, 0.76 g (5.5 mM) anhydrous $K_2CO_3$, and 5 ml dimethylformamide was heated to 150° and stirred for 15 min. While still fairly warm, the stirred mixture was treated dropwise with water until the initial deposit of KBr dissolved and the product began to crystallize. It was filtered off, dried (crude yield 90%), and recrystallized by dissolving in a minimum quantity of hot acetone and precipitating with twice its volume of petroleum ether. The light yellow crystals of XIX had m.p. 143°–144°.

COMPOUND XX 1-(2-amino-4-benzyloxyphenoxy)-2-(2'-amino-5'-methylphenoxy)ethane (XX) was prepared as follows:

5 g (11.8 mmole) XIX and 0.5 g of 5% platinum on charcoal were suspended in 100 ml absolute ethanol and stirred under hydrogen. The theoretical volume was taken up in 5 hrs. but the mixture was left under hydrogen overnight, after which the cumulative uptake was 19% higher than theoretical. Another 5 g of XIX added to the same hydrogenation mixture also took up the same higher-than-theoretical amount of hydrogen overnight. The product XX was recrystallized from acetone and had melting point 129°–132°. The NMR spectrum showed that the benzyl groups had not been lost. ($CDCl_3 + CD_3SOCD_3$, 90 MHz): 7.29, s, 5H; 6.75–6.45, m, 4H; 6.32, d, 3 Hz, 1H; 6.12, dd, 3 Hz +7 Hz, 1H; 4.93, s, 2H; 4.3, br s, 4.26, s, total 4H; 2.27, s, 3H.

COMPOUND XXI 1-(2-amino-4-benzyloxyphenoxy)-2-(2'-amino-5'-methylphenoxy)ethane-N,N,N',N'-tetracetic acid, tetraethyl ester (XXIV) was prepared as follows:

3.64 g (10 mmole) XX, 10.72 g (50 mmole) 1,8-bis(-dimethylamino)naphthalene, 2.0 g (13 mmole) dried NaI, 8.35 g (50 mmole) ethyl bromoacetate, and 15 ml acetonitrile were stirred and refluxed under nitrogen for 40 hrs, with a further addition of 1.5 ml ethyl bromoacetate and 2 g 1,8-bis(dimethylamino)naphthalene after the first 24 hrs. The cooled reaction mixture was evaporated to dryness, diluted with toluene and filtered; the gray precipitate was washed repeatedly with further small portions of toluene. The pooled toluene solutions were repeatedly extracted with phosphate buffer until the washings had the same pH (2) as the fresh buffer. The toluene solution was then washed with water and dried over $MgSO_4$. After evaporation of the toluene under reduced pressure, the residue was washed with petroleum ether-ethyl acetate 9:1 v/v to remove traces of ethyl bromoacetate. The yield of XXI was 6.4 g (90%), m.p. 95°–96°.

COMPOUND XXII 1-(2-amino-4-hydroxy-phenoxy)-2-(2'-amino-5'-methylphenoxy)ethane-N,N,N',N'-tetraacetic acid, tetraethyl ester (XXII) was prepared as follows:

XXI was debenzylated by hydrogenation in glacial acetic acid with 5% Pd on charcoal catalyst at atmospheric pressure.

Acetoxymethyl bromide

Acetoxymethyl bromide, $CH_3COOCH_2Br$, was prepared by stirring 4.0 g (30 mM) methylene diacetate and 5.0 g (33 mM) trimethylsilyl bromide, in the presence of 60 mg anhydrous $ZnCl_2$ but no added solvent, for 48 hr at room temperature. The product was distilled crudely at 10 torr, 40°–60° then refractionated through a Vigreaux column at 10 torr, 55°–57°, yielding 4.04 g, 87%, containing no detectable $BrCH_2OCH_2Br$ by NMR. Lewis acid catalysis is essential; without it there is no reaction even at 110° in a sealed tube overnight. Methylene diacetate was prepared from paraformaldehyde and acetic anhydride (see Knoevenagel, E., 1913) and was carefully distilled to remove $CH_3COOCH_2OCH_2OCOCH_3$.

EXAMPLES

Specific properties and embodiments of the present invention are outlined in the following examples. Such examples are for illustrative purposes only and are not intended to limit the scope of the claims in any way.

EXAMPLE I

Chemical tests

Nitr-1 and nitr-2 were tested in vitro by diluting the saponification solutions to final chelator concentrations of between 4 and 50 micromole in aqueous buffers containing 100 mmole KCl and known $Ca^{2+}$ concentrations ranging from $<10^{-10}$ M to $>10^{-3}$ M. The choice of chelator concentration was merely to give convenient optical densities in 1 cm cuvets. Although these compounds will photolyze upon illumination with ultraviolet light, the UV spectrophotometer used was found to use low enough light levels so that measuring absorbance spectra caused negligible photochemical reaction. UV absorbance spectra of separate samples of nitr-1, nitr-2, and nitr-3, titrated with buffered $Ca^{2+}$ solutions, were measured, avoiding significant exposure to ultraviolet light. A family of such curves is shown in FIG. 3 for the titration of nitr-2 with $Ca^{2+}$. Using these curves and others (not shown), the $Ca^{2+}$ dissociation constants of each of nitr-1, nitr-2, and nitr-3 were determined to be about 160 nM.

Other samples of nitr-1, nitr-2, and nitr-3, plus either 1 mM EDTA or EGTA or 1 mM $Ca^{2+}$, were irradiated at 254 or 365 nm using a hand mercury lamp fixed at a known distance from the sample, which was stirred in a 1 cm UV cuvette. UV spectra were measured periodically to follow the photolysis reaction. Illumination intensities were measured by ferrioxalate actinometry (see Hatchard, et al., 1956) and approximately confirmed by a bolometer (Yellow Springs Instrument Co. YSI-65A). FIG. 4 illustrates representative curves showing changes seen in the absorbtion spectrum of 4 microM nitr-2, illuminated at 365 nm in EGTA and no $Ca^{2+}$. With each dye, photolysis caused a large increase in extinction near 370–380 nm, which is attributed to conjugation of the amino nitrogen with the ketone moiety. For example, the extinction coefficient of nitr-2 irradiated in zero [$Ca^{2+}$] increases from 3500 to 17,500 $M^{-1}cm^{-1}$ at 380 nm (see FIG. 4). With illumination intensity of $7.8 \times 10^{-9}$ einsteins·$cm^{-2}$·$sec^{-1}$ (1 einstein = $6.02 \times 10^{23}$ photons) at 365 nm, the time course of the change in extinction coefficient was a decaying exponential whose time to reach 90% completion was about 20 min (see FIG. 2), indicating a quantum efficiency of about 0.03. If a sample of nitr-2 is photolysed in high [$Ca^{2+}$], the change in absorbance (FIG. 5) is less marked at 370–380 nm but is most pronounced at 320 nm, at which the extinction coefficient changes from 2800 to 11,600 $M^{-1}cm^{-1}$. This change requires somewhat less total exposure to 365 nm irradiation, 6 min for 90% completion, corresponding to a quantum efficiency of 0.1. The measured quantum efficiencies of nitr-3 for photolysis with 365 nm light were 0.015 with no calcium and 0.042 with 1 mM $Ca^{2+}$ (data not shown).

After photolysis, dissociation constants of each compound were determined by titrating photolyzed samples of nitr-1, nitr-2, and nitr-3 with $Ca^{2+}$. FIG. 6 shows a representative family of spectra for Ca²⁺ titration of nitr-2 after photolysis (compare with FIG. 3). Each photolyzed compound was found to have a dissociation constant for $Ca^{2+}$ in the range of 6-10 microM, representing substantially weaker (40-60 fold) binding than before photolysis. With nitr 2 it was possible to confirm that 365 nm photolysis yielded the same covalent rearrangement whether carried out in high or low [$Ca^{2+}$], i.e., raising [$Ca^{2+}$] then photolysing resulted in the same spectrum as photolysing in low [$Ca^{2+}$], then raising [$Ca^{2+}$]. Nitr-1 was not so well behaved, due possibly to impurities or to the more generally destructive effects of the 254 nm radiation used.

The stable states of nitr-2 can be summarized by the diagram shown in Table I.

Summary

Thus it can be seen that the present invention discloses novel photolabile $Ca^{2+}$ chelators that store $Ca^{2+}$ in a physiologically inactive form until illuminated with ultraviolet light, whereupon the $Ca^{2+}$ tends to be released. This released $Ca^{2+}$ is then free to activate physiological processes. Since the new chelators disclosed herein make it possible to now use light to control the release of $Ca^{2+}$ inside cells they will be extremely useful to biological researchers trying to study the many cellular functions that calcium is now believed to control.

It can also be seen that the present invention discloses an improved method for synthesizing 1-hydroxy- or

TABLE I

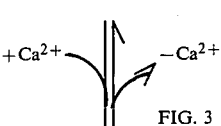

lambda max in nm (extinction coefficient)
Q = quantum efficiency.
The FIGS. referred to in the diagram above relate to the associated processes shown graphically in FIGS. 3-6.

EXAMPLE II

Biological Tests

To demonstrate one use of photolabile $Ca^{2+}$ chelators disclosed herein a representative compound (nitr-2) was used to show changes in membrane conductance. It is well known that increasing intracellular free [$Ca^{2+}$] causes changes in potassium current (see Meech, (1978) for a review). This current can be detected either by showing an increase of negativity in the membrane potential, or by direct measurement of the current when the membrane potential is held constant by a voltage clamp technique. Both of these methods were used by Dr. R. S. Zucker, who tested nitr-2 in a single neuron preparation (L2 in the abdominal ganglion) in the sea hare *Aplysia californica*. A solution was injected into the cell to give approximately 8 mM nitr-2 and 6 mM $Ca^{2+}$. The transmembrane potential was then measured. When the cell was illuminated with light from a 75 watt xenon lamp, there was hyperpolarization of about 0.9 mV (see FIG. 7). This change is not due to the effects of the light on the preparation, since uninjected control cells showed no response to the illumination.

In another experiment, measuring current under voltage clamp conditions (−45 mV) showed a small outward current due to illumination of a similarly injected cell (see FIG. 8). Again, the uninjected control cell showed no such change.

1-alkoxy-1-(2-nitroaryl)-1-aryl methanes. Methanes of this type are either critical to the preparation of, or actually constitute, the photolabile $Ca^{2+}$ chelating compounds disclosed and discussed herein.

Various modifications of the invention in addition to those shown and described herein will become apparent to those skilled in the art from the foregoing description and accompanying drawings. Such modifications are intended to fall within the scope of the appended claims.

What is claimed is:

1. A chemical compound having the general formula:

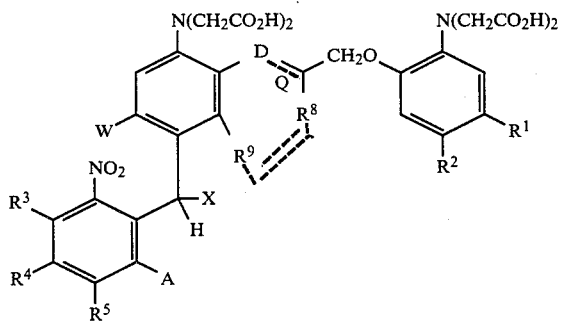

and the pharmaceutically acceptable non-toxic salts and esters thereof wherein:

A is —NO₂ or —H;

$R^1$ is selected from the group comprised of —H (unless $R^2$ is also H), —CH$_3$, —F, —Cl, and —Br;

$R^2$ is selected from the group comprised of —H (unless $R^1$ is also H), —CH$_3$, —F, —Cl, —Br, C$_1$-C$_4$ alkoxy;

$R^3$, $R^4$ and $R^5$ are independently —H, OH, NR$^6$R$^7$, or alkoxy, or $R^3$ and $R^4$ together are —OCH$_2$O— or —OCH$_2$CH$_2$O— and $R^5$ is —H, OH, NR$^6$R$^7$, or alkoxy, or $R^4$ and $R^5$ together are —OCH$_2$O— or OCH$_2$CH$_2$O— and $R^3$ is —H, OH, NR$^6$R$^7$, or alkoxy;

X is selected from the group comprised of —OH, alkoxy, —Cl, —Br, —NR$^6$R$^7$, —OCOCH$_3$, —OCOCF$_3$, —OCOCH$_2$NH$_2$, —OPO$_3$H, and —OSO$_2$CH$_3$;

$R^6$ and $R^7$ are independently —H, methyl or ethyl;

D is O, N, NH, or N alkyl;

Q is a double bond when D is N and a single bond otherwise;

$R^8$ is H and $R^9$ is H or $R^8$ and $R^9$, together with heteroatom D, the carbon adjacent $R^8$, and the phenyl ring adjacent to $R^9$, form a quinoline ring system (D=N, Q=double bond); and W is —H, —OH, or —NHR$^6$, or alkoxy.

2. A chemical compound having the general formula:

and the pharmaceutically acceptable non-toxic salts and esters thereof wherein:

A is —NO$_2$ or —H;

$R^3$, $R^4$ and $R^5$ are independently —H, OH, NR$^6$R$^7$, or alkoxy, or $R^3$ and $R^4$ together are —OCH$_2$O— or —OCH$_2$CH$_2$O— and $R^5$ is —H, OH, NR$^6$R$^7$, or alkoxy, or $R^4$ and $R^5$ together are —OCH$_2$O— or —OCH$_2$CH$_2$O— and $R^3$ is —H, OH, NR$^6$R$^7$, or alkoxy;

X is selected from the group comprised of —OH, alkoxy, —Cl, —Br, —NR$^6$R$^7$, —OCOCH$_3$, —OCOCF$_3$, —OCOCH$_2$NH$_2$, —OPO$_3$H, and —OSO$_2$CH$_3$;

$R^6$ and $R^7$ are independently —H, methyl or ethyl;

D is O, N, NH, or N alkyl;

Q is a double bond when D is N and a single bond otherwise;

$R^8$ is H and $R^9$ is H or $R^8$ and $R^9$, toghether with heteroatom D, the carbon adjacent to $R^8$, and the phenyl ring adjacent to $R^9$, form quinoline ring system (D=N, Q=double bond); and W is —H, —OH, or NHR$^6$, or alkoxy.

3. The compound of claim 1 wherein said tetraacetic acid esters are alpha-acyloxyalkyl esters.

4. The compound of claim 3 wherein said alpha-acyloxyalkyl esters are acetoxymethyl esters.

5. The compound of claim 1 wherein $R^2$ is methyl.

6. The compound of claim 1 wherein D=O and $R^8$=$R^9$=H.

7. The compound of claim 2 wherein said tetraacetic acid esters are alpha-acyloxyalkyl esters.

8. The compound of claim 7 wherein said alpha-acyloxyalkyl esters are acetoxymethyl esters.

9. The compound of claim 2 wherein $R^2$ is methyl.

10. The compound of claim 2 wherein D=O and $R^8$=$R^9$=H.

11. The compound 1-(2-amino-5-(1-methoxy-1-(2-nitrophenyl)methyl)-phenoxy)-2-(2'-amino-5'-methylphenoxy)ethane-N,N,N',N' tetraacetic acid.

12. The compound 1-(2-amino-5-(1-methoxy-1-(2-nitro-4,5-methylenedioxyphenyl)methyl)-phenoxy)-2-(2'-amino-5'-methylphenoxy)-ethane-N,N,N',N'-tetraacetic acid.

13. The compound 1-(2-amino-5-(1-methoxy-1-(2,6-dinitro-3-methoxyphenyl))methylphenoxy)-2-(2'-amino-5'-methylphenoxy)-ethane,N,N,N',N' tetraacetic acid.

* * * * *

UNITED STATES PATENT AND TRADEMARK OFFICE
CERTIFICATE OF CORRECTION

PATENT NO. : 4,689,432
DATED : August 25, 1987
INVENTOR(S) : Roger Y. Tsien, Et al.

It is certified that error appears in the above-identified patent and that said Letters Patent is hereby corrected as shown below:

In the Abstract, line 14, "prcursors" should be --precursors--.

Column 2, line 50, "nitr 1" should be --nitr-1--.

Column 5, line 20, in diagram, "A" should be --X--.

Column 13, line 35, "$44°14\ 45°$" should be --$44°-45°$--.

Column 19, line 6, "nitr 2" should be --nitr-2--.

Column 19, line 17, Table I, " a nitrobenzophenone" should be -- a nitrosobenzophenone --.

Column 21, line 37, "A" should be --X--.

Column 8, line 47, "XXI to XXI" should be --XXI to XXII--.

Column 16, line 13, "XIX" should be --XVI--.

Signed and Sealed this

Second Day of February, 1988

Attest:

DONALD J. QUIGG

Attesting Officer

Commissioner of Patents and Trademarks